United States Patent [19]

Luoma, II

[11] Patent Number: 5,271,852
[45] Date of Patent: Dec. 21, 1993

[54] CENTRIFUGAL METHOD USING A PHASE-SEPARATION TUBE

[75] Inventor: Robert P. Luoma, II, Newark, Del.

[73] Assignee: E. I. Du Pont de Nemours and Company, Wilmington, Del.

[21] Appl. No.: 877,497

[22] Filed: May 1, 1992

[51] Int. Cl.⁵ .................................... B01D 21/26
[52] U.S. Cl. .................................... 210/789; 210/787; 210/800; 210/516; 422/101; 436/177
[58] Field of Search ............... 210/515, 516, 518, 787, 210/800, 789; 422/72, 101; 436/177

[56] References Cited

U.S. PATENT DOCUMENTS

| | | |
|---|---|---|
| 3,468,474 | 9/1969 | Shoblom et al. |
| 3,741,400 | 6/1973 | Dick ............................ 210/516 |
| 3,813,031 | 5/1974 | Anderson . |
| 3,849,072 | 11/1974 | Ayres ........................... 23/259 |
| 3,852,194 | 12/1974 | Zine, Jr. ......................... 210/83 |
| 3,929,646 | 12/1975 | Adler ............................ 210/359 |
| 3,941,699 | 3/1976 | Ayres ............................ 210/117 |
| 3,957,197 | 5/1976 | Sartory et al. . |
| 3,957,654 | 5/1976 | Ayres ............................ 210/516 |
| 4,001,122 | 1/1977 | Griffin ........................... 210/516 |
| 4,021,352 | 5/1977 | Sarstedt ......................... 210/359 |
| 4,083,784 | 4/1978 | Zine, Jr. . |
| 4,083,788 | 4/1978 | Ferrara .......................... 210/516 |
| 4,135,883 | 1/1979 | McNeil et al. .................... 422/72 |
| 4,151,844 | 5/1979 | Cullis et al. ..................... 128/214 R |
| 4,152,269 | 5/1979 | Babson .......................... 210/516 |
| 4,152,270 | 5/1979 | Cornell ......................... 210/516 |
| 4,154,690 | 5/1979 | Ballies .......................... 210/516 |
| 4,202,769 | 5/1980 | Greenspan . |
| 4,203,840 | 5/1980 | Stoeppler et al. . |
| 4,269,718 | 5/1981 | Persidsky ....................... 210/787 |
| 4,278,202 | 7/1981 | Westberg . |
| 4,283,276 | 8/1981 | Grant ............................ 209/155 |
| 4,284,602 | 8/1981 | Kelton et al. .................... 422/72 |
| 4,285,810 | 8/1981 | Kirkland et al. .................. 209/155 |
| 4,350,585 | 9/1982 | Johansson et al. ................. 210/94 |
| 4,350,593 | 9/1982 | Kessler .......................... 210/516 |
| 4,417,981 | 11/1983 | Nugent .......................... 210/209 |
| 4,443,345 | 4/1984 | Wells ............................ 210/782 |
| 4,522,713 | 6/1985 | Nussbaumer et al. ............... 210/136 |
| 4,530,691 | 7/1985 | Brown ........................... 494/45 |
| 4,534,465 | 8/1985 | Rothermal et al. ................. 206/443 |
| 4,550,084 | 10/1985 | Nelson et al. .................... 436/45 |
| 4,557,719 | 12/1985 | Neumann et al. .................. 494/37 |
| 4,639,316 | 1/1987 | Eldegheidy ...................... 210/416.1 |
| 4,724,317 | 2/1988 | Brown et al. .................... 250/231 SE |
| 4,828,716 | 5/1989 | McEwen et al. ................... 210/740 |

FOREIGN PATENT DOCUMENTS 184274 6/1986 European Pat. Off. .

*Primary Examiner*—Robert A. Dawson
*Assistant Examiner*—David Reifsnyder

[57] ABSTRACT

A method of partitioning a pre-selected phase of a sample of liquid having a plurality of phases of differing densities, and a tube. A sample of liquid is passed through a first end of a linear tube and into a first chamber of said tube. The first chamber is located at the first end of the tube and is separated from a second chamber located at a second opposed end of the tube by a separation device. The separation device slidably engages the interior surface of the tube in an essentially fluid-tight manner and has a flow-restriction orifice therein to permit fluid flow communication between the first and second chambers under the influence of force. The phases are then ordered within the tube using e.g. axial centrifugation. The volume of the first chamber is reduced by movement of the separation device within the tube, such that one phase of the liquid in the first chamber flows through the flow-restriction orifice and into the second chamber.

4 Claims, 2 Drawing Sheets ded by the
CENTRIFUGAL METHODS USING A PHASE-SEPARATION TUBE

FIELD OF THE INVENTION

The present invention relates to a method and apparatus for the separation into phases of a sample of liquid, including colloidal suspensions, having a plurality of phases of differing densities, and especially for the separation of one phase of the liquid sample from the remainder of the liquid in a manner that minimizes contamination of the phases and contamination of a phase of the liquid with the liquid per se. The invention is particularly useful in the separation of blood into components thereof, especially for purposes of testing and analysis of blood components, while minimizing contamination of a separated phase by the whole blood.

BACKGROUND OF THE INVENTION

Diagnostic tests frequently require separation of a patient's whole blood sample into components, especially cellular portions from non-cellular portions e.g. serum or plasma from cells. For instance, plasma is obtained from anticoagulated blood and still contains all of the coagulation proteins, whereas serum is obtained from clotted blood with the proteins being retained with the clot and red blood cells. Samples of whole blood are typically collected by ventipuncture through a special cannula or needle attached to a syringe or an evacuated collection tube. The sample of blood in the form that is to be separated into components is typically drawn, using a needle, through a penetrable self-sealing elastomericclosure or other stopper into an evacuated tube. Separation is then accomplished e.g. by rotation of the tube in a conventional centrifuge e.g. a swinging bucket or a fixed angle centrifuge, as the different components of the whole blood have different densities, as described in U.S. Pat. No. 4,152,269 of A.L. Babson.

An apparatus and method of separating blood phases by rotation of a tube about its longitudinal axis i.e. axial rotation, are described in U.S. Pat. No. 4,828,716 of J.A. McEwen et al. The blood sample is introduced to the tube through a cap assembly that consists of a pierceable closure and a separator that has a one-way valve. The tube is then rotated about its longitudinal axis; the heavier cellular phase lines the tube wall and thereby separates from the lighter non-cellular (plasma or serum) phase. Once separation has been achieved, an axial probe penetrates the pierceable closure, detaches the separator from the closure and forces the separator down the tube. The axially-located non-cellular phase passes through the separator. An optical sensor is utilized to detect when the cellular phase begins passing into the separator, and to stop movement of the separator. Thus, the two phases are physically separated. However, it is believed that a separator that is more reliable in operation and which may be manufactured in a cost effective manner is required. A separator of different design that is believed to be effective in maintaining the phases in a physically separated form is disclosed in the copending application of G.A. Adams and R.P. Luoma, filed concurrently herewith.

In the separation of a liquid, especially blood, into phases, it is important that cross-contamination of samples be minimized and preferably avoided. In particular, whole blood should not contaminate serum fractions, as can occur in tubes conventionally used in the trade.

SUMMARY OF THE INVENTION

Accordingly, the present invention provides a method of partitioning a pre-selected phase of a sample of liquid having a plurality of phases of differing densities, comprising the steps of: (a) passing said sample of liquid through a first end of a linear tube and into a first chamber of said tube, said first chamber being located at the first end of said tube and being separated from a second chamber located at a second opposed end of said tube by a separation device, said second chamber being free of the liquid, said separation device slidably engaging the interior surface of the tube in an essentially fluid-tight manner and having a flow-restriction orifice therein to permit fluid flow communication between the first and second chambers under the influence of force; (b) ordering the phases of the sample within the tube using axial centrifugation; and (c) while the phases are ordered, reducing the volume of the first chamber by movement of the separation device within the tube, such that one phase of the liquid in the first chamber flows through the flow-restriction orifice as the volume of the first chamber is reduced and into the second chamber, said phase in the second chamber being removable therefrom through the second end of the tube.

In a preferred embodiment of the method of the invention, the flow-restriction channel permits flow of liquid from the first chamber to the second chamber during step (c) but restricts flow of liquid at other times.

The present invention additionally provides a method of partitioning a pre-selected phase of a sample of liquid having a plurality of phases of differing densities, comprising the steps of: (a) passing said sample of liquid through a first end of a linear tube and into a first chamber of said tube, said first chamber being located at the first end of said tube and being separated from a second chamber located at a second opposed end of said tube by a separation device, said second chamber being free of the liquid, said separation device slidably engaging the interior surface of the tube in an essentially fluid-tight manner and having a flow-restriction orifice therein to permit fluid flow communication between the first and second chambers under the influence of force; and (b) ordering the phases of the sample within the tube using centrifugal force.

The present invention also provides a tube for the partitioning and separation of a pre-selected phase of a sample of liquid having a plurality of phases of differing densities, said tube having a separation device located within the tube that separates the tube into at least two chambers at opposed ends of the tube, said separation device slidably engaging the interior surface of the tube in an essentially fluid-tight manner and having an orifice therethrough for fluid flow communication between the chambers, said orifice having a flow-restriction channel, and said tube having sealable openings at both of the opposed ends of said tube.

In embodiments of the invention, the second chamber is an incipient chamber that forms as the separation device is moved along the tube.

DESCRIPTION OF THE DRAWINGS

The invention will be described with particular reference to the drawings in which.

DETAILED DESCRIPTION

Figure 1:
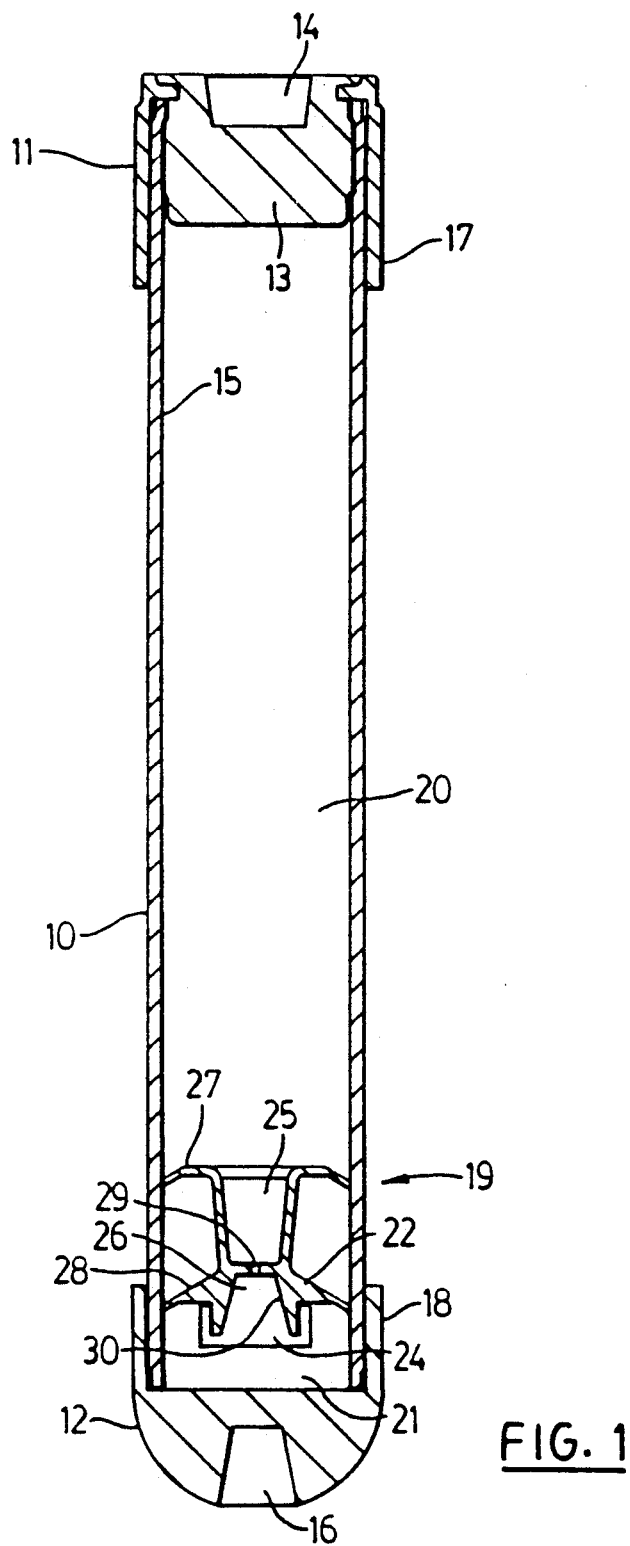
FIG. 1 is a schematic representation of a cross-sectional area of one embodiment of the tube.

Referring to FIG. 1, tube 10 (which may also be known as or referred to as a vial) is shown as having a first end cap 11 and a second end cap 12. As shown, the end caps are of different construction. Tube 10 has a substantially constant diameter, and constant cross-section, throughout a major portion of its length. First end cap 11 is comprised of a plug 13 having recess 14. Plug 13 fits inside tube 10 and forms a fluid and vacuum tight seal with the inner surface 15 of tube 10, so as to form a fluid tight closure with tube 10. First end cap 11 also has rim 17 that fits tightly onto the outside of tube 10. In addition, the exposed end of first end cap 11 is shown as having a flat end, which could be used to stand the tube in a vertical position. In contrast, second end cap 12 is shown as having a rounded exposed end. The shape of the end of end caps 11 and 12 is not critical to the invention; the presence of two opposed end caps is essential to the invention, as discussed herein.

Second end cap 12 is shown as having recess 16, which is axially located in the end cap. In addition, second end cap 12 has rims 18 which fit over the end of tube 10 to form a fluid and gas tight seal therewith. It will be appreciated that there are variations in the type of end cap that may be used. In embodiments, the end cap is accompanied by a stopper or plug, with the stopper or plug providing the fluid and gas tight seal and the end cap being for protection and/or to retain the stopper or plug in place.

The separation device in tube 10 is generally indicated by 19. Separation device 19 divides the space within tube 10 into first chamber 20 and second chamber 21; it is to be understood that in embodiments of the invention, end cap 12 contacts and seats with separation device 19 such that second chamber 21 is in effect an incipient chamber which forms into chamber 21 on movement of separation device 19 within tube 10. Separation device 19 is comprised of separation shell 22 and plug 24. Separation shell 22 has a first shell recess 25 disposed towards first chamber 20 and second shell recess 26 disposed towards second chamber 21; first shell recess 25 may contain a filter (not shown). Separation shell 19 also has first flange 27 and second flange 28, which in the embodiment shown are non-planar curved surfaces that extend to and are in sliding engagement with inner wall 15 of tube 10, and form an effective fluid tight seal therewith; flanges of other shapes may be used. While two flanges are shown, and are preferred, it is believed that at least one flange is required. Plug 24 is located in second shell recess 26. The inner surface 30 has a convoluted path formed in the surface thereof which, in conjunction with the surface of plug 24, forms a channel (not shown) that is in fluid flow communication between opposite ends of plug 24. Separation shell 19 is shown as having an axial orifice 29 for flow of fluid.

The space between first flange 27 and second flange 28 is used for monitoring of the separation process. While optical monitoring of the process is a preferred method, other methods e.g. infrared and ultrasonic, may be used.

Plug 24 would normally be made from an elastomeric material with requirements with respect to a method of operation described herein. during movement of the separation device 19 within tube 10. End caps will normally be relatively rigid plastic, depending on whether penetration by needles is required. Plugs or stoppers may be rigid or elastomeric, including self-sealing elastomeric, again depending on the particular intended mode of operation. The self-sealing materials referred to herein, especially with respect to the end caps, are known in the art of blood collection tubes.

Figure 2:
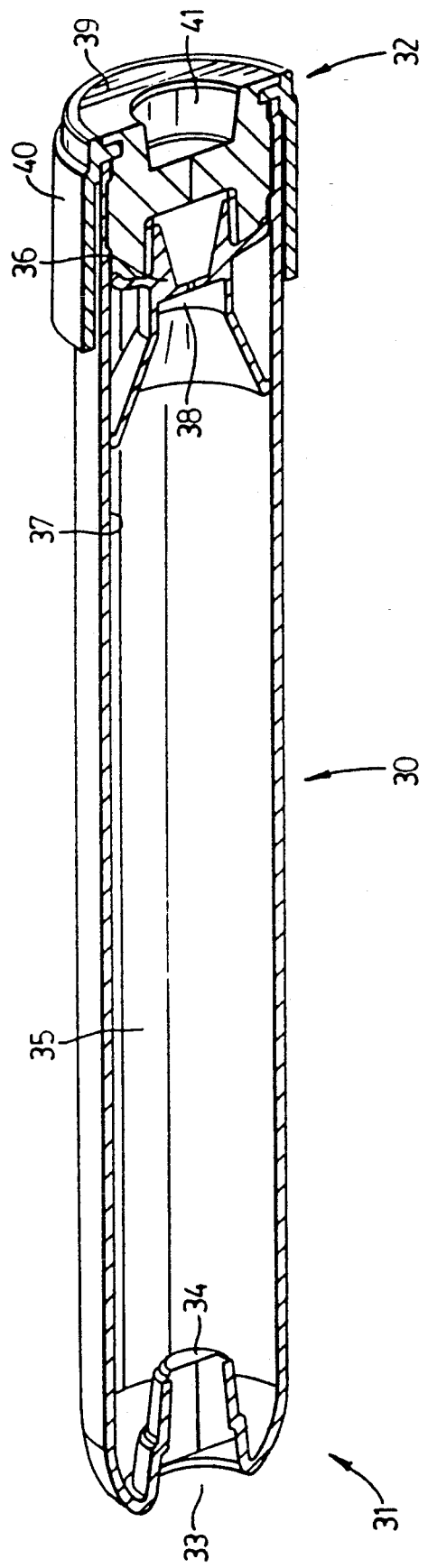
FIG. 2 is a schematic representation of a cross-sectional area of another embodiment of the tube.

FIG. 2 shows another embodiment of the tube. Tube 30 has a first end 31 and a second end 32. First end 31 is shown as having a recessed orifice 33 containing plug 34. Recessed orifice 33 is shown as being moulded as part of first end 31, and is located on the longitudinal axis of tube 30. First chamber 35 is located between plug 34 and separation device 36. Separation device 36 is in sliding engagement with wall 37 of tube 30, and has axial orifice 38 for flow of fluid from first chamber 35 to a second chamber. In the embodiment shown in FIG. 2, the second chamber is an incipient chamber that forms on movement of separation device 36 along tube 30 towards first end 31, but the second chamber could exist at all times. As shown, the incipient second chamber is located between, and at the mating surface of, separation device 36 and end cap 39 in second end 32. End cap 39 has lips 40 that fit over the outside of tube 30 and hold end cap 39 in position, as well as end cap recess 41 which is used during movement of the separation device and removal of fluid from the tube. It will be noted that end cap 39 has a flat end, whereas second end cap 12 of FIG. 1 has a rounded end; these shapes represent two embodiments of the end caps that may be used.

FIG. 1 and FIG. 2 show two different types of end caps adjacent to the first chamber viz. first end cap 11 and recessed orifice 33 with plug 34. It is to be understood that other end caps may be used, including grommets, the principal requirement being that the resultant tube meet all physical, functional and regulatory requirements for the intended use.

Embodiments of the separation device are described in greater detail in the copending patent application of G.A. Adams and R.P. Luoma filed concurrently herewith.

In operation, a sample of liquid having phases of differing densities e.g. blood, is placed in the tube; the operation of the method of the invention will generally be described herein with reference to separation of blood into a cell fraction and a non-cellular fraction. The blood is inserted into first chamber 20. In the embodiment of FIG. 1, this may be done by removing first end cap 11 and inserting the blood. However, for safety reasons, blood is normally drawn directly into first chamber 20, as a consequence of having a vacuum inside first chamber 20, using a needle.

The separation device is particularly intended for use in an axial centrifuge e.g. an axial centrifuge of the type described in the aforementioned U.S. Pat. No. 4,828,716. The separation device is rotated about its longitudinal axis to effect phase separation. When separation is complete, the high viscosity, concentrated, clotted cells are located near the tube wall and the lower viscosity non-cellular fraction e.g. serum (and any air or other gases) are located closer to the longitudinal axis. A probe then penetrates second end cap 12 and contacts and is resisted by plug 24. Further force by the probe causes the separation device to become detached from second end cap 12 and to move along tube 11, thereby decreasing the volume of first chamber 20. This decrease in volume results in the material located on the longitudinal axis flowing through access channel 29, along the convoluted path located at the interface between plug 24 and separation shell 19 and into second chamber 21. Air or other gaseous matter is the first to flow into second chamber 21, followed by the non-cellular fraction. An optical (or other) sensor is located exterior to the tube and is able to monitor the separation device as it moves along the tube. When blood cells enter shell recess 26, the movement of the probe, and hence the separation device 19, ceases, and thus the blood cells do not enter second chamber 21. The probe is withdrawn while the tube is still being rotated about its axis, with the result that the probe does not become contaminated by the sample in the tube. Thus, it is believed that the probe is capable of being used on a subsequent sample without cross-contamination of samples.

A similar mode of operation is used for the embodiment of FIG. 2.

The tube is made of an optically transparent material e g. glass or Selar ® polyamide, which is manufactured by E.I. du Pont de Nemours and Company of Wilmington, Delaware U.S.A. Other optically transparent materials may be used, prime requirements being acceptable transparency and sufficient strength to withstand the forces applied in a centrifugation process. In addition, the tube must be capable of retaining a vacuum, a capability of retention of vacuum for a period of about 2 years being preferred. Tubes or vials of acceptable properties are known and used in the collection and processing of blood. The separator shell may be moulded from thermoplastic or other polymers, a prime requirement being that the polymer not have adverse effects on the properties and characteristics of the blood and the components thereof. The separation device needs to be optically transparent, if optical means are to be used for the monitoring and control of the method of separation of the liquid into phases. Otherwise, a material suitable for the particular monitoring method is required. In addition, the separation device needs to provide an adequate fluid seal against the side of the tube in which it is located, and be capable of being fabricated into the shape of the separation device. An example of a suitable material is polypropylene.

The material used in the fabrication of the plugs will depend in particular on mode of operation of the process. In the method particularly described herein, a probe exerts pressure on plug 24 in order to move the separation device along the tube. Such pressure must not cause blockage of passages used for flow of fluid from the first chamber to the second chamber, and the material selected for fabrication of the plug must take this requirement into account. In addition, the material of the plug must not adversely affect the fluid in the tube or results of any tests or analyses conducted on that fluid or its components. Ethylene/vinyl acetate polymer compositions have been found to be acceptable, including Elvax ® 250, 260, 450 and 550 polymer compositions available from E.I. du Pont de Nemours and Company, but other compositions will become apparent to persons skilled in the art; it is believed that polypropylene, polycarbonate and stainless steel could be used.

The end caps need to be made from a self-sealing material, especially a self-sealing elastomeric material. Examples of such materials are known in the art.

It is preferable that fluid not flow back from second chamber 21 into first chamber 20 after the centrifuging, especially axial centrifuging, of the tube has ceased, but it is more important that fluid not continue to flow, albeit intermittently, from first chamber 20 into second chamber 21. In particular, it is important that in-use handling, including shaking and tipping of the tube, does not result in flow of fluid in either direction, especially not flow of the cell fraction from chamber 20 into chamber 21. Fluid flow paths having such characteristics are known, for example the convoluted path described in the aforementioned copending application of G.A. Adams and R.P. Luoma.

The double-ended separation tube of the present invention has a minimal number of independent parts, resulting in few critical mating surfaces and connections, for improved consistency and reliability from tube to tube. A particularly important aspect of the invention is that the drawing of blood or other fluid into the tube is physically separated from the removal of samples from the tube. Thus, the blood is drawn into one of the tube and the samples are withdrawn from the other end of the tube. This eliminates possible contamination of the sample by blood as a result of droplets of blood remaining in or on plugs or end caps, or the like, through which needles are passed during drawing of blood; in the present invention this occurs at the opposite ends of the tube, thereby eliminating that source of contamination. A practical tube accomplishing this advantage is described herein, especially with respect to axial centrifugation separation processes. Another advantage, especially compared with the tube described in the aforementioned copending application of G.A. Adams and R.P. Luoma, is that the physical requirements imposed on the plug, especially with respect to distortion of the plug and blocking of fluid flow channels during movement of the separation device using a probe, are significantly reduced. Potential problems associated with passage of needles through the plug during drawing of samples are eliminated.

A filter may be used in first shell recess 25 to filter fluid passing through that recess to the axial orifice. For example, platelets could be filtered from the blood fraction passing through the axial orifice.

It is understood that the tubes may contain anticoagulants or clot activators, as is known in the art.

Although the tube and separation device have been described herein with reference to axial centrifugation, at least some tubes and separation devices described herein are also capable of being used in conventional centrifuges. It is to be understood, however, that the separation device may not function in the manner described herein. even though the tube containing the separation device is usable.

I claim:

1. A method of partitioning a pre-selected phase of a sample of liquid having a plurality of phases of differing densities, comprising the steps of:
   (a) passing said sample of liquid through a first end of a linear tube and into a first chamber of said tube, said first chamber being located at the first end of said tube and being separated from a second chamber located at a second opposed end of said tube by a separation device, said separation chamber being free of the liquid, said separation device slidably engaging the interior surface of the tube in an essentially fluid-tight manner an having a flow-restriction orifice therein to permit fluid flow communication between the first and second chambers under the influence of force;
   (b) ordering the phases of the sample within the tube by rotating the tube about its longitudinal axis; and
   (c) while the phases are ordered, reducing the volume of the first chamber by movement of the separation device within the tube, such that one phase of the liquid in the first chamber flows through the flow-restriction orifice as the volume of the first chamber is reduced and into the second chamber, said phase in the second chamber being removable therefrom through the second end of the tube.

2. The method of claim 1 in which the flow-restriction channel permits flow of liquid from the first chamber to the second chamber during step (c) but restricts flow of liquid at other times.

3. The method of claim 1 in which the second chamber is an incipient chamber that forms as the separation device is moved along the tube.

4. The method of claim 1 in which serum or plasma is separated.

* * * * *